United States Patent [19]

Seo

[11] Patent Number: 4,993,417
[45] Date of Patent: Feb. 19, 1991

[54] METHOD AND SYSTEM FOR CONTROLLING ULTRASOUND SCANNING SEQUENCE

[75] Inventor: Yasutsugu Seo, Ootawara, Japan

[73] Assignee: Kabushiki Kaisha Toshiba, Kawasaki, Japan

[21] Appl. No.: 423,713

[22] Filed: Oct. 18, 1989

Related U.S. Application Data

[63] Continuation of Ser. No. 228,590, Aug. 5, 1988, abandoned.

[30] Foreign Application Priority Data

Aug. 12, 1987 [JP] Japan ............................... 62-201244

[51] Int. Cl.$^5$ .............................................. A61B 8/06
[52] U.S. Cl. ................................................ 128/661.09
[58] Field of Search ......... 128/660.05, 661.07–661.10; 73/861.25

[56] References Cited

U.S. PATENT DOCUMENTS

| | | | |
|---|---|---|---|
| 4,583,552 | 4/1986 | Iinuma | 128/661.09 |
| 4,612,937 | 9/1986 | Miller | 128/661.09 X |
| 4,660,565 | 4/1987 | Shirasaka | 128/661.09 |

FOREIGN PATENT DOCUMENTS

| | | |
|---|---|---|
| 0190979 | 8/1986 | European Pat. Off. |
| 3417418 | 11/1985 | Fed. Rep. of Germany |
| 3605163 | 8/1986 | Fed. Rep. of Germany |
| 3614688 | 10/1986 | Fed. Rep. of Germany |

Primary Examiner—Francis Jaworski
Attorney, Agent, or Firm—Cushman, Darby & Cushman

[57] ABSTRACT

The sequence for a case of scanning by an ultrasound prove having a plurality of transducers, for example, m numbers, is as follows: first scan line→(m−1)th scan line→mth scan line→first scan line→second scan line→mth scan line→first scan line→second scan line→third scan line→first scan line→. . . The ultrasound probe transmits ultrasound beams to a subject and receives echo signals reflected from the subject in accordance with the above sequence. Doppler signals obtained from the echo signals are stored in a memory. When the predetermined number of Doppler signals in each line are stored in the memory, the Doppler signals in each line are read out from the memory. By such scanning sequence, a repeat frequency, i.e., a sampling frequency of Doppler signals of the ultrasound beams transmitted in the same direction, is a shorter. As a result, a low limit of measurable flow velocity is a lower, and a timing for reading out (outputting) the Doppler signals from the memory can be a constant.

7 Claims, 10 Drawing Sheets

ULTRASOUND
TRANSMITTING
PULSE SIGNAL

RECEIVING
ECHO SIGNAL

PHASE DETECT
OUTPUT SIGNAL $$\frac{e_O}{e_{in}} = \frac{(Z-1)^2}{Z^2-(K1+K2)Z+K1}$$

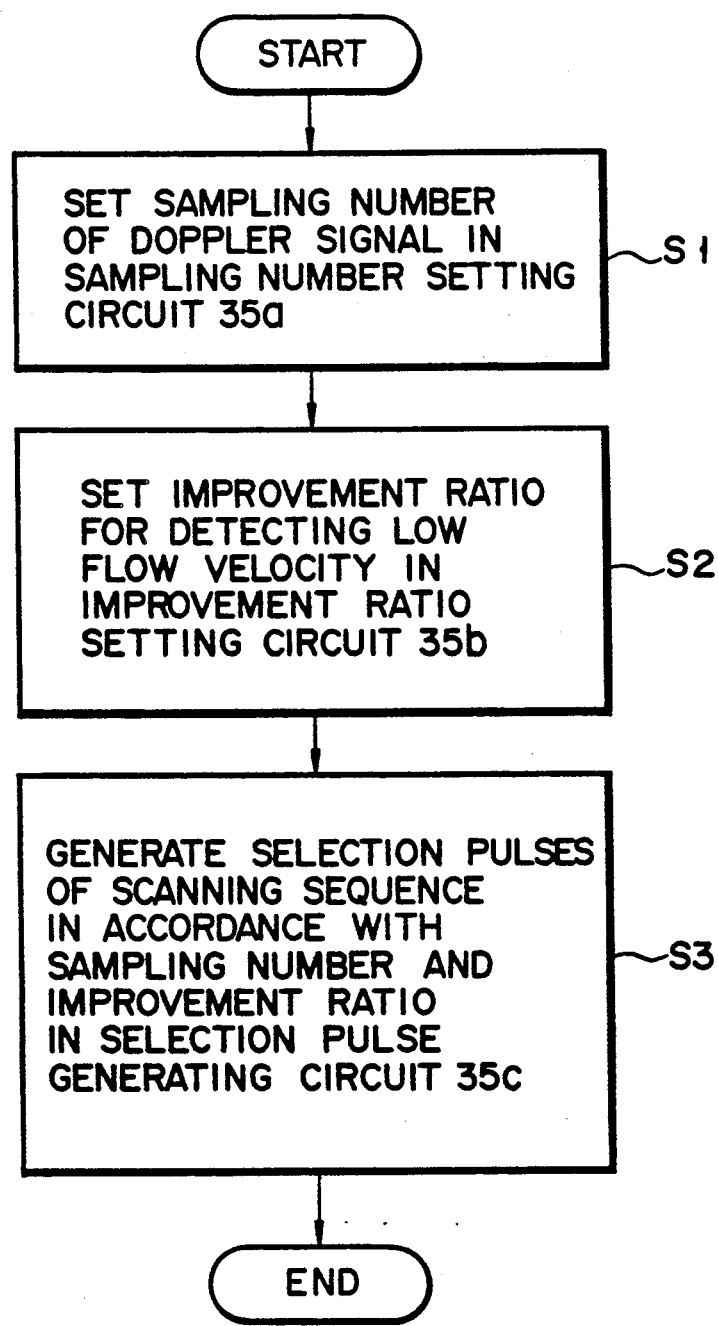
F I G. 10

METHOD AND SYSTEM FOR CONTROLLING ULTRASOUND SCANNING SEQUENCE

This is a continuation of application Ser. No. 07/228,590, filed Aug. 5, 1988, and now abandoned.

BACKGROUND OF THE INVENTION

1. Field of the Invention

The present invention relates to a method and system for controlling ultrasound scanning sequence so as to permit detection of a low flow velocity.

2. Description of the Related Art

Conventionally, an apparatus has been used which combines the ultrasonic Doppler method and the pulse echo method to acquire a blood-flow image and a tomogram image (B-mode image) of a subject under examination and displays the acquired images in colors in real time. The principle of measurement of blood-flow velocity used in the apparatus will be described hereinafter.

When ultrasound beams are transmitted to blood flowing within the living body of a subject, the beams are scattered by moving blood cells so that the center frequency fc of the beams is Doppler-shifted by a Doppler frequency fd. As a result, the received ultrasound frequency f becomes $f = fc + fd$. In this case, the Doppler frequency fd is represented by $$fd = 2v \cos \theta \times fc/c \quad \ldots (1)$$

where v is a blood flow velocity, $\theta$ is an angle made by the ultrasonic beam with the blood vessel, and c is the acoustic velocity. It will thus be understood that the Doppler frequency fd is used to detect the blood flow velocity v in this way.

The blood flow velocity v is displayed in a two-dimensional form as follows. First, as shown in FIGS. 1 and 2, ultrasound probe 1 transmits ultrasound beams sequentially to the subject in directions of A, B, C, . . . by pulse signals provided from transmitting circuit 7 under the sector-scan control. In place of the sector-scan control the linear-scan control may be performed.

For example, echo signals of the ultrasound beams transmitted in the direction of A, which has been Doppler-shifted by the blood flow, are received by ultrasonic probe 1 and applied to receiving circuit 2 after conversion of an electric signal. Phase detecting circuit 3 detects Doppler signals from the received echo signals. The Doppler signals at, for example, 256 sampling points along a scan line (in the direction A) of the ultrasound beam transmitted are detected. The Doppler signals detected at each sampling point are frequency-analyzed in frequency analyzer 4 and then provided to display 6 via digital scan converter (DSC) 5. As a result, a blood-flow-velocity distribution image in the direction of A is displayed in real time.

Subsequently, the same operations are repeated for each of the scan directions of B, C, . . . , and blood-flow-velocity distribution images for scan directions are displayed as a two-dimensional image.

It is to be noted that the detectability of a blood flow velocity depends upon the data length of a Doppler signal. That is to say, if the sampling frequency of the Doppler signal is fr and the number of samples is n, then the data length T of the Doppler signal will be given by $$T = n/fr \quad \ldots (2)$$

In this case, the frequency resolution $\Delta fd$ will become $$\Delta fd = 1/T \quad \ldots (3)$$

Therefore, the Doppler frequency fd min corresponding to the measurable lower limit of the flow velocity will be represented by $$fd\ min = 1/T = fr/n \quad \ldots (4)$$

Therefore, it will be understood that either the sampling frequency fr of the Doppler signal has to be lowered, or the sampling number n has only to be increased (see FIGS. 3 and 4, FIG. 4 is obtained by fourier-transforming the waveform shown in FIG. 3), in order to detect the blood flow of a low velocity.

In the two-dimensional Doppler blood-flow imaging, the next relationship holds.

$$Fn \times n \times m \times (1/fr') = 1 \quad \ldots (5)$$

where Fn is the number of frames displayed in one second, m is the number of scan lines and fr' is the repetition frequency of the ultrasound pulses. The frame number Fn is associated with the real-time display of a two-dimensional blood flow image and usually takes a value between 8~30 so that 8~30 frames will be displayed in one second. For example, in the sector scan as shown in FIG. 5, when the scan line number m=32, the repetition frequency fr' of ultrasound pulses=4 KHz, and the sampling number n=8, the frame number Fn will become about 16. That is, if the scan line number m increases, the frame number Fn decreases, causing flicker. If the scan line number decreases, the density of scan lines would become coarse and hence the quality of image would be degraded.

Therefore, an apparatus has been desired which is capable of detecting a low flow velocity without decreasing the number of frames and degrading the image quality.

SUMMARY OF THE INVENTION

It is an object of the present invention to provide a method and system for controlling the ultrasonic scanning sequence to permit the detection of a low flow velocity.

According to one aspect of the present invention, there is provided a method for controlling ultrasound scanning sequence, the method comprising the steps of:

setting a sampling number of Doppler signals in a same direction;

setting an improvement ratio used for detecting a low flow velocity of the subject; and controlling the ultrasound scanning sequence by generating transducer selection signals in accordance with the sampling number of the Doppler signals and the improvement ratio, so as to decrease a sampling frequency of the Doppler signals without changing an ultrasound pulse repetition frequency.

According to another aspect of the present invention, there is provided a system for controlling ultrasound scanning sequence, the system comprising:

transmitting means for transmitting ultrasound beams to a subject;

receiving means for receiving echo signals reflected from the subject by the ultrasound beams transmitted by the transmitting means;

detecting means for detecting Doppler signals from the echo signals received by the receiving means;

storing means for storing the Doppler signals detected by the detecting means; and control means for controlling the transmitting means, the receiving means and the storing means in accordance with the ultrasound scanning sequence, so as to decrease a sampling frequency of Doppler signals without changing an ultrasound pulse repetition frequency.

BRIEF DESCRIPTION OF THE DRAWINGS

FIG. 10 is a flowchart of operations of the control circuit;

FIG. 15 is a timing diagram of the third type of scanning sequence.

DETAILED DESCRIPTION OF THE PREFERRED EMBODIMENT

Figure 1:
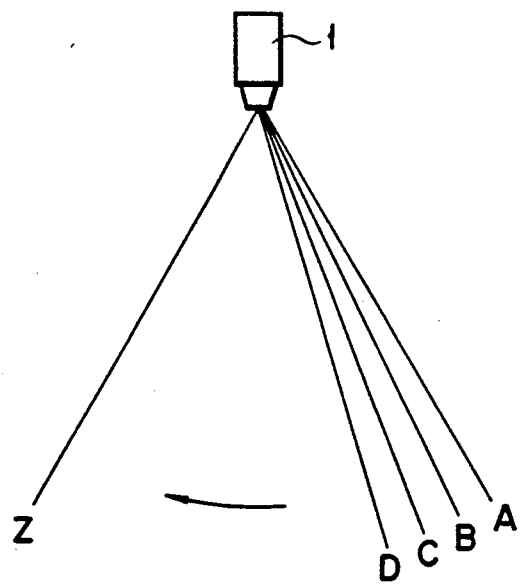
FIG. 1 shows a conventional scanning pattern.
Figure 2:
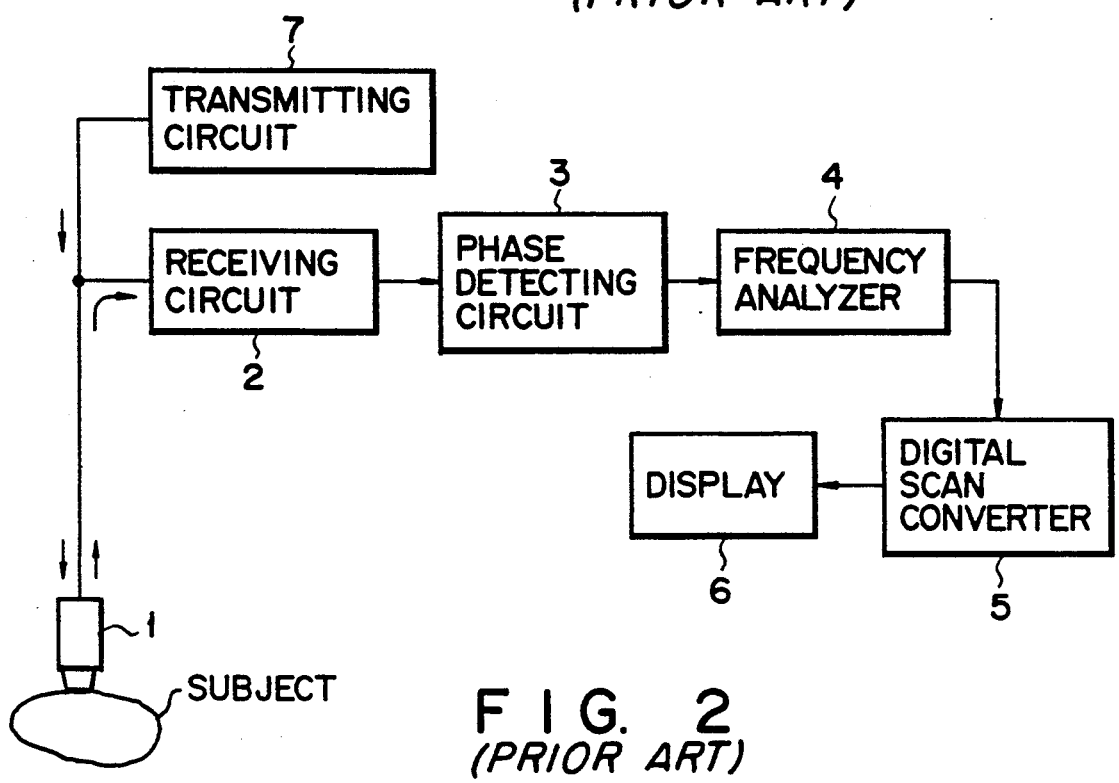
FIG. 2 is a block diagram of a conventional ultrasonic diagnostic apparatus.
Figure 3:
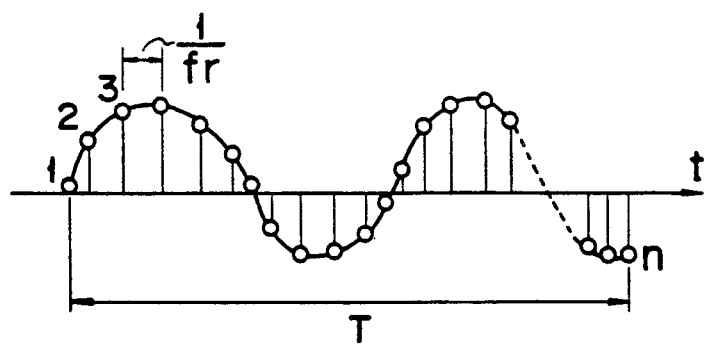
FIGS. 3 and 4 are diagrams for explaining the data length and frequency resolution of a Doppler signal.
Figure 4:
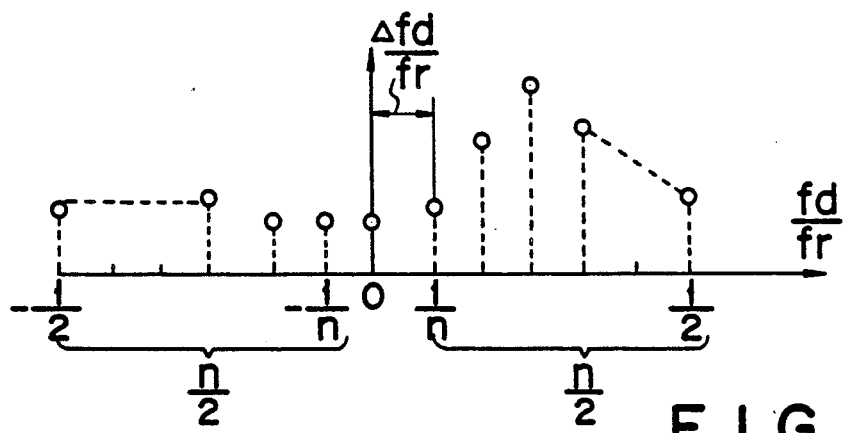
Figure 5:
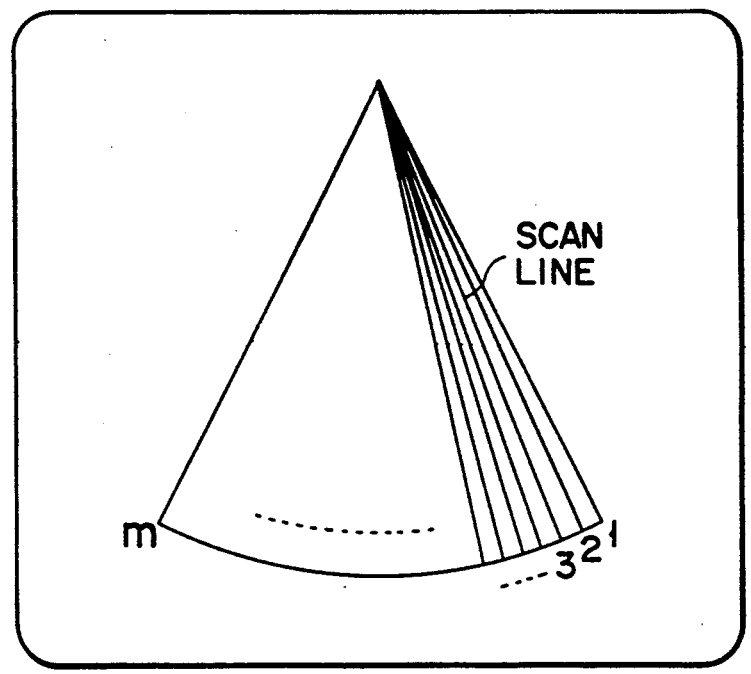
FIG. 5 is a diagram for explaining a sector scan.
Figure 6:
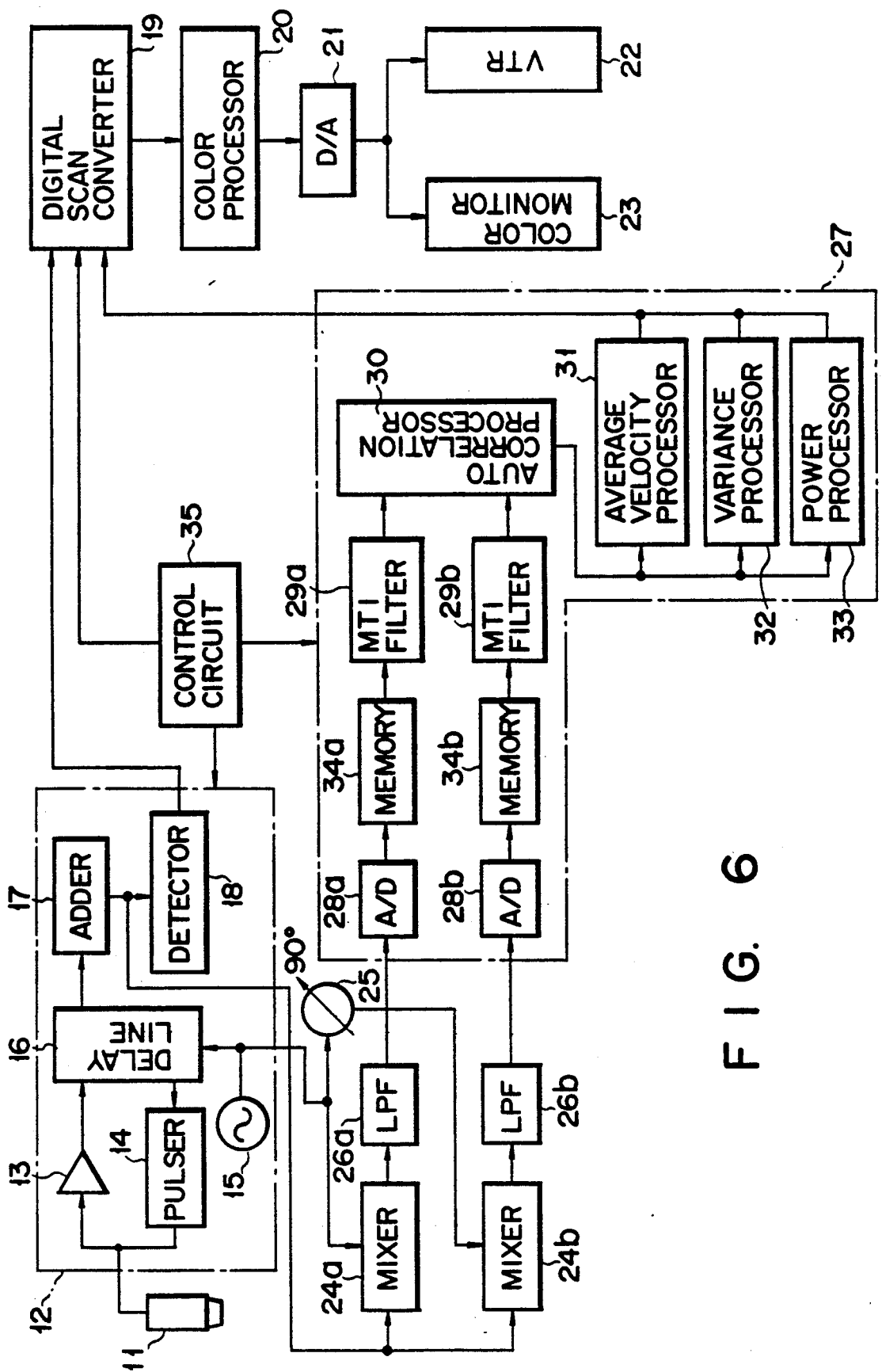
FIG. 6 is a system block diagram of an embodiment of the present invention.

Referring now to FIG. 6, sector-scan analog section 12 comprises preamplifier 13, pulser 14, oscillator 15, delay line 16, adder 17 and detector 18, and ultrasonic probe 11 transmits and receives ultrasound beams to and from a subject under examination.

Control circuit 35 controls ultrasonic scanning sequence in sector-scan analog section 12 so as to lower a sampling frequency of a Doppler signal without changing a repetition frequency of ultrasound pulses. Control circuit 35 comprises a central processing unit (CPU), and a programmable read only memory (PROM) and the like.

A signal provided from adder 17 is applied, via detector 18, DSC 19, color processor 20, digital/analog converter 21, to color monitor 23 and video tape recorder (VTR) 22. An ultrasound tomogram image (B-mode image) is displayed on color monitor 23.

The signal provided from adder 17 is also used for displaying an ultrasound blood flow image and hence applied to mixers 24a and 24b. In mixer 24a, the output signal of adder 17 is multiplied by a reference signal of a reference frequency fo provided by oscillator 15, while, in mixer 24b, the output signal of adder 17 is multiplied by a 90-degree phase-shifted reference signal from 90-degree phase shifter 25 connected to oscillator 15. As a result, the frequency component of fd of a Doppler signal and a high frequency component of (2fo+fd) are obtained. The frequency components are applied to low pass filters (LPFs) 26a and 26b so as to remove the high frequency component (2fo+fd), and the frequency component fd of the Doppler signal only is obtained in LPFs 26a and 26b. The Doppler signal is used as a phase detect output signal for ultrasonic blood flow imaging.

Figure 7A:
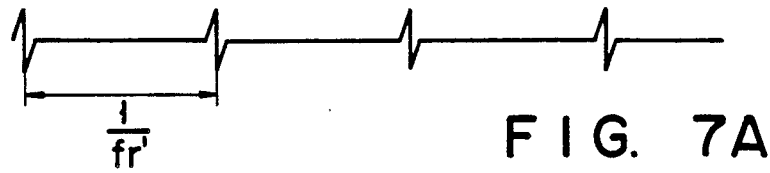
FIGS. 7A through 7C show signal waveforms in principal part of the embodiment system.
Figure 7B:
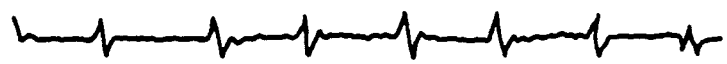
Figure 7C:

FIGS. 7A to 7C, FIG. 7A shows an ultrasound transmitting pulse signal transmitted to the subject from ultrasound probe 11, FIG. 7B shows a receiving echo signal reflected from the subject, and FIG. 7C shows a phase detect output signal.

The phase detect output signal contains not only components associated with blood flow but also unwanted components resulting from reflection from slowing moving objects (clutters) such as heart walls. To remove the unwanted components, the phase detect output signal is applied to moving target indicator (MTI) processing unit 27.

MTI processing unit 27 comprises A/D converters 28a and 28b, memories 34a and 34b, MTI filters 29a and 29b, auto correlation processor 30, average velocity processor 31, variance processor 32 and power processor 33.

A/D converters 28a and 28b convert output signals of LPFs 26a and 26b to digital signals, respectively. The digital signals are applied to memories 34a and 34b, respectively. Memories 34a and 34b each store Doppler signals for a plurality of scanning lines in accordance with the ultrasound scanning sequence under the control of control circuit 35.

Figure 8:
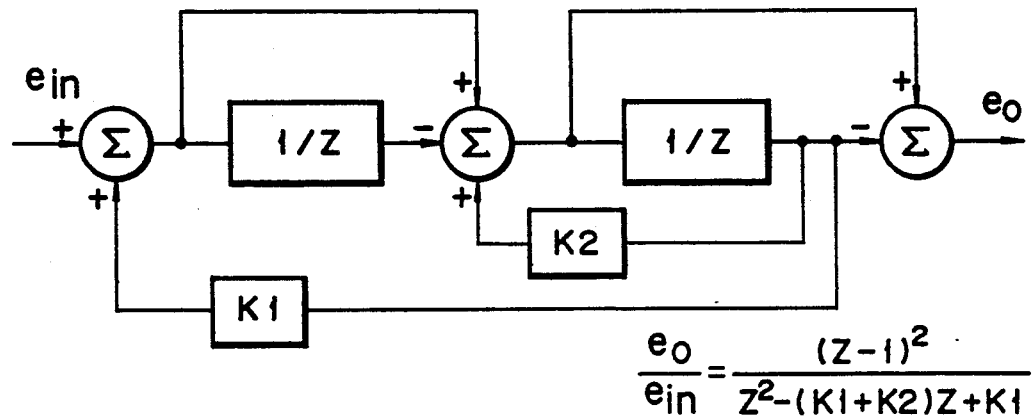
FIG. 8 shows an arrangement of an MTI filter used with the embodiment system.

FIG. 8 shows an arrangement of the MTI filter, in which 1/Z is for a delay of one rate, Σ is a summation, and k1 and k2 are each a coefficient.

Auto correlator processor 30 is used for performing, in real time, frequency analysis for multipoints of two dimensions.

Average velocity processor 31 calculates an averaged Doppler frequency $\overline{fd}$ on the basis of the following equation.

$$\overline{fd} = \int f \times s(f) df / \int S(f) df \qquad \ldots (6)$$

where S(f) is a power spectrum.

Variance processor 32 calculates variance $\sigma^2$ on the basis of the following equation.

$$\sigma^2 = \int f^2 \times S(f) df / \int S(f) df - (\overline{fd})^2 \qquad \ldots (7)$$

Power processor 33 calculates a power TP on the basis of the following equation.

$$TP = \int S(f) df \qquad \ldots (8)$$

The power TP is proportional to the intensity of echoes scattered from blood cells. Echoes from moving objects corresponding to frequencies below the cut-off frequency of the MTI filter are eliminated.

Values of the average velocity, variance and power calculated at each sample point are applied to DSC 19 and, after the interpolation processing, converted to color data in color processor 20. In the case of velocity-variance ($\overline{v} - \sigma^2$) display, the flow in the direction approaching to ultrasound probe 11 is converted to, for example, a red color, while the flow in the direction leaving from ultrasound probe 11 is converted to a blue color. The average velocity is represented by differences in brightness, and the velocity variance is indicated by a hue (mixed with green).

Next, the operation of the system of the present invention will be described.

Figure 9:
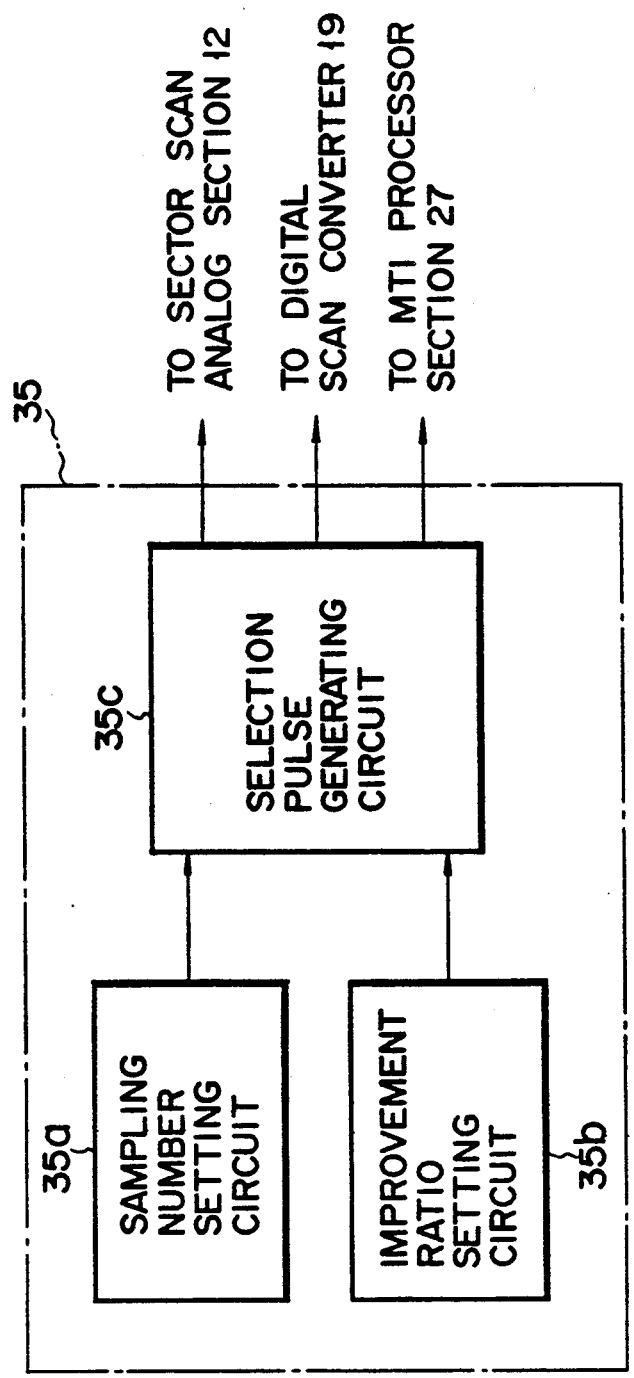
FIG. 9 shows an arrangement of a control circuit used with the embodiment system.

In the present system, the control of the ultrasound scanning sequence is performed by control circuit 35. As shown in FIG. 9, control circuit 35 comprises sampling number setting circuit 35a for setting the sampling number n of the same scanning line, improvement ratio setting circuit 35b for setting an improvement ratio P to improve the detectability of a low flow velocity, and selection pulse generating circuit 35c for generating a pulse signal to select a scanning sequence. Selection pulse generating circuit 35c determines a scan line and the timing of a transmitting pulse signal in accordance with the sample number n and the improvement number P set by setting circuits 35a and 35b, and outputs the pulse signal at the determined time to sector scan analog section 12, DSC 19 and MTI processing unit 27.

Control circuit 35 is comprised of CPU, PROM and the like as described above and has functions by circuits shown in FIG. 9. The operations of the control circuit will be described with reference to a flowchart shown in FIG. 10.

As shown in FIG. 10, in step S1, the sampling number n of a Doppler signal is set in sampling number setting circuit 35a. In step S2, the improvement ratio P used for detecting a low flow velocity is set in improvement ratio setting circuit 35b. In step S3, the scanning sequence selection pulse signal is generated in selection pulse generating circuit 35c in accordance with the sampling number n and the improvement ratio P set in steps S1 and S2.

In practice, the control of the scanning sequence is performed as follows.

Figure 11:
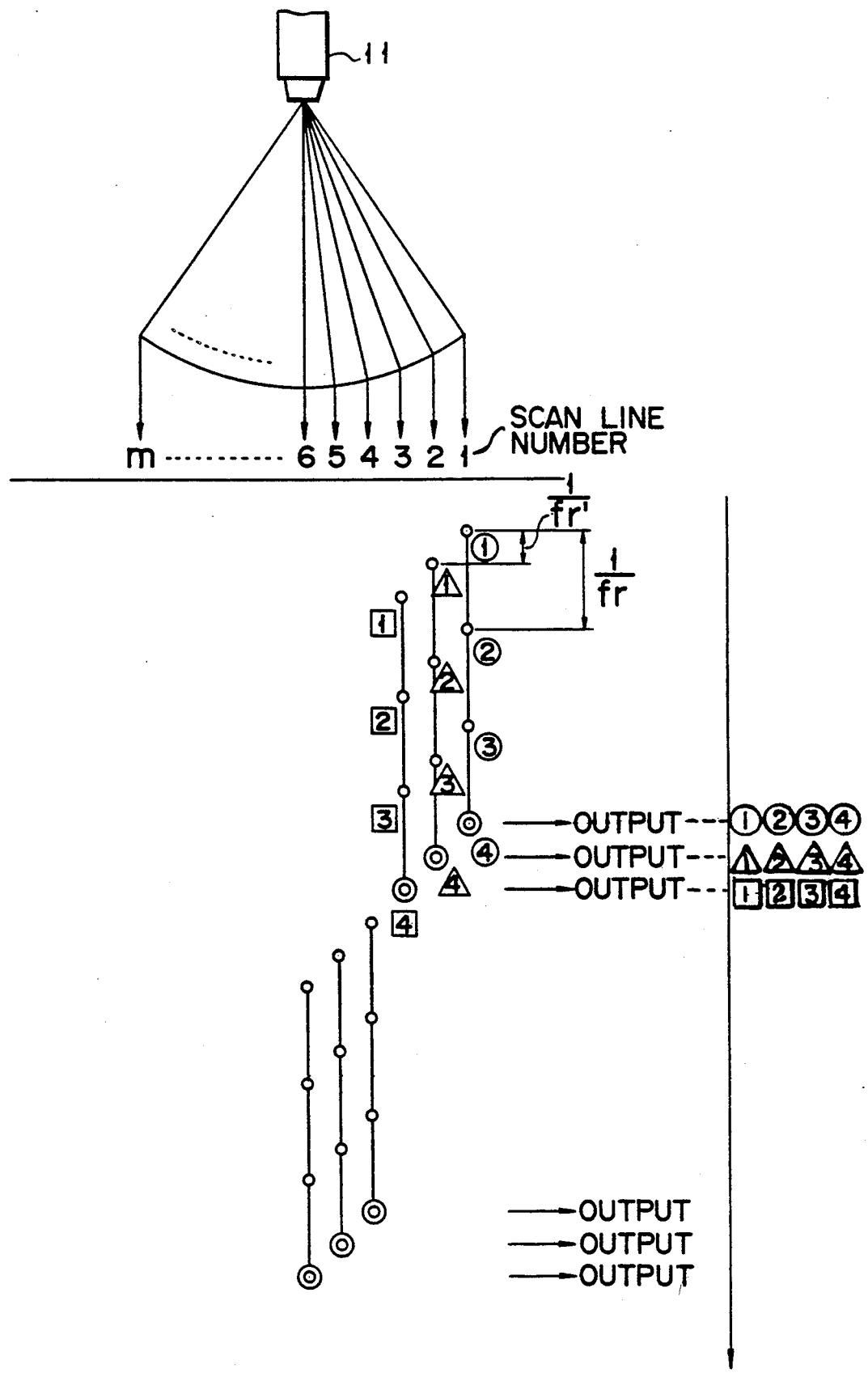
FIG. 11 shows a first type of scanning sequence used with the control circuit.

As shown if FIG. 11, in the sequence where an ultrasound beam is first transmitted from the right end of ultrasound probe 11, the scanning is performed in sequence of the first scan line at the right end, the second scan line, the third scan line, and the first scan line at the right end, and so on. In this case (P=3), the repetition frequency fr of the ultrasound beam (the sampling frequency of a Doppler signal) transmitted in the same direction becomes $$fr = fr'/3 \qquad \ldots (9)$$

As can be seen from equation (4), the frequency fd min corresponding to the lower limit of the measurable flow velocity decreases to one third compared with a conventional method where an ultrasound beam is transmitted n times along a scan line, and similarly an ultrasound beam is transmitted n times along the next adjacent scan line.

In the case of FIG. 11, the time of transmission of the ultrasound beam in the same direction, i.e., the sampling number n of the Doppler signal, is four. Thus, the ultrasound beam is transmitted and received in accordance with the ultrasound scanning sequence, and the Doppler signal is stored in memories 34a and 34 b. When the fourth data (n=4) is stored in memories 34a and 34b for each of scan lines, the four pieces of data for each of the scan lines are read out from memories 34a and 34b. In the case of FIG. 11, the readout of the four pieces of data for each of scan lines is not performed at equal intervals, complicating the timing control for data readout.

Figure 12:
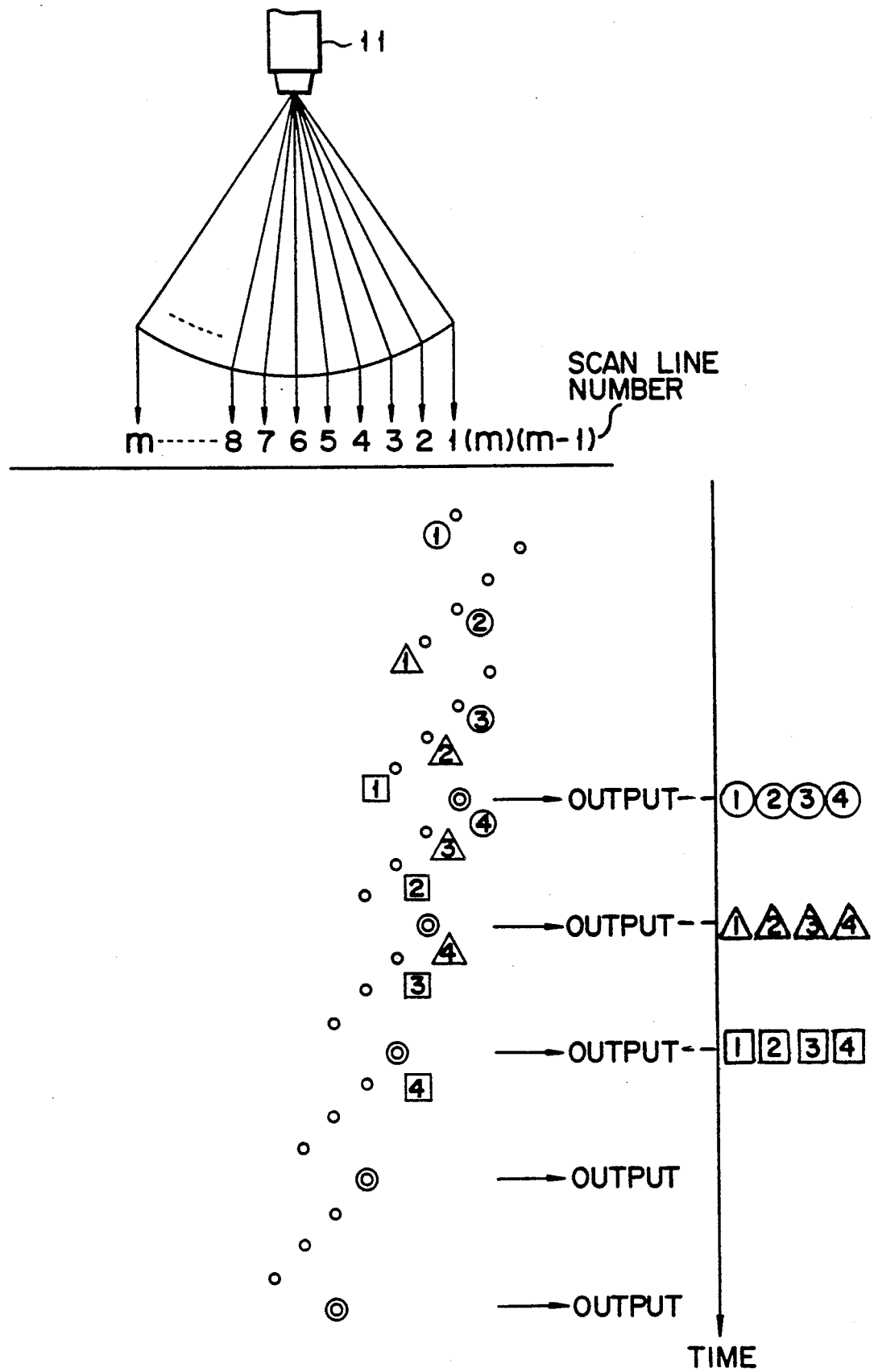
FIG. 12 shows a second type of scanning sequence used with the control circuit.
Figure 13:
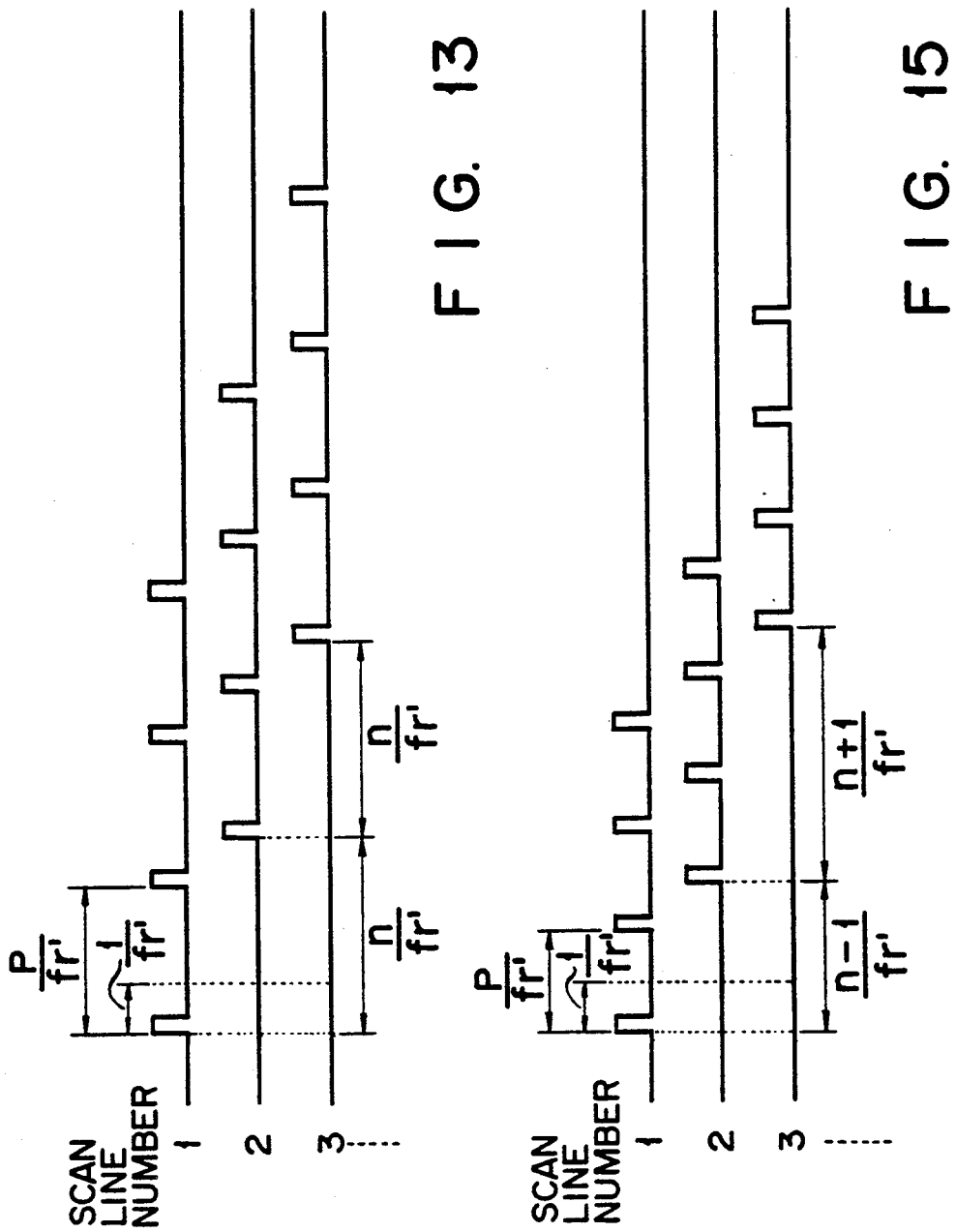
FIG. 13 is a timing diagram of the second type of scanning sequence.

To perform the readout of data for each of scan lines at nearly equal intervals, such scanning sequence as shown in FIGS. 12 and 13 may be utilized. That is, in the case of the scan starting from the right end of ultrasound probe 11 the scan may be performed in sequence of the first scan line, the (m−1)-th scan line, the m-th scan line, the first scan line, the second scan line, the m-th scan line, the first scan line, the second scan line, the third scan line, the first scan line, and so on. According to the scanning sequence, the repetition frequency (the sampling frequency of Doppler signal) fr of ultrasound beam transmitted in the same direction decreases to $\frac{1}{3}$, and the data stored in memories 34a and 34b can be read out at equal time intervals.

In general, by the repetition frequency fr of an ultrasound beam transmitted in the same direction and the repetition frequency fr' of an ultrasound transmitting pulse, the improvement ratio P for the detectability of a low flow velocity is represented by $$P = fr'/fr \qquad \ldots (10)$$

FIGS. 11 and 12 show a case where P=3.

Figure 14:
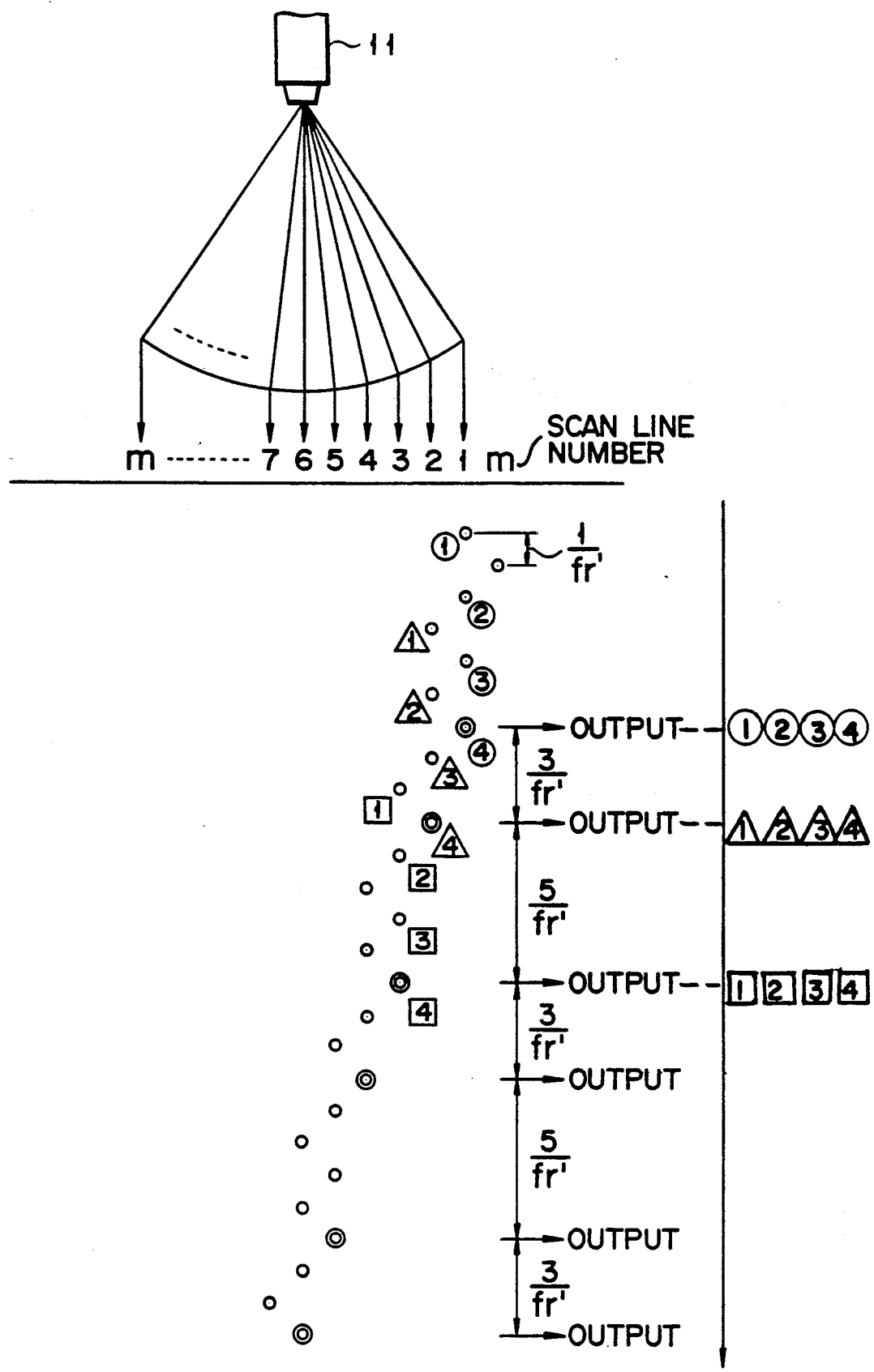
FIG. 14 shows a third type of scanning sequence used with the control circuit.

It is to be noted that, when P is an integral multiple of n, the data stored in memories 34a and 34b cannot be read out at equal time intervals. FIG. 14 shows scanning sequence and its timing diagram for data readout in the case of n=4 and P=2, for example. As can be seen from the drawings, the data stored in memories 34a and 34b is read out at different time intervals of 3/fr', 5/fr', 3/fr', 5/fr', ...

The blood flow information obtained by the scanning sequence as described above and B-mode image is applied to color monitor 23 through DSC 19, color processor 20 and D/A converter 21. The blood flow information and the B-mode image may be recorded by VTR 22 as needed.

As described above, by controlling the ultrasound scanning sequence in the embodiment of the present invention, the sampling frequency fr of the Doppler signal can be decreased without changing the repetition frequency fr' of the ultrasound pulse. Therefore, the blood flow of a low velocity also can be detected without decreasing the frame number Fn and degrading the image quality.

Although the preferred embodiment of the present invention has been described and disclosed, it is apparent that other embodiments and modifications of the invention are possible.

What is claimed is:

1. A method for controlling an ultrasound scanning sequence, the method comprising the steps of:
    setting a number of ultrasound beams transmitted to a subject in a same direction;
    setting a detection ratio used for detecting a flow velocity of the subject; and
    controlling the ultrasound scanning sequence in accordance with the number of ultrasound beams and the detection ratio, so as to increase a transmission interval of the ultrasound beams in the same direction without changing a generation interval of an ultrasound pulse.

2. A method according to claim 1, wherein the detection ratio P is obtained by the following equation:

$$P = fr'/fr$$

where fr is a frequency corresponding to a transmission interval of the ultrasound beams in the same direction and fr' is the frequency corresponding to the generation interval of ultrasound pulse.

3. A method as in claim 1, wherein said controlling step includes the steps of, in sequence:
   (a) commanding transmitting an ultrasound beam to the subject in a first direction;
   (b) commanding transmitting ultrasound beams to the subject in additional directions, including a second direction through a direction having a number equal to said detection ratio; and
   (c) repeating said steps (a) and (b) a number of times equal to said generation interval.

4. A system for controlling an ultrasound scanning sequence, the system comprising:
   transmitting means for transmitting ultrasound beams to a subject;
   receiving means for receiving echo signals from the subject;
   processing means for processing echo data representing the received echo signals to obtain a flow velocity;
   storing means for storing the echo data; and
   control means for controlling the transmitting means, the receiving means and the storing means in accordance with the ultrasound scanning sequence, so as to increase a transmission interval of the ultrasound beams in the same direction without changing a generation interval of an ultrasound pulse.

5. A system according to claim 4, wherein the detection ratio P is obtained by the following equation:

$$P = fr'/fr$$

where fr is the frequency corresponding to the transmission interval of the ultrasound beams and fr' is the frequency corresponding to the generation interval of ultrasound pulse.

6. A system according to claim 5, wherein the control means includes:
   first setting means for setting a number of ultrasound beams transmitted to a subject in the same direction:
   second setting means for setting a detection ratio used for detecting a flow velocity of the subject; and
   generating means for generating control signals for controlling the ultrasound scanning sequence by the number set by the first setting means and the detection ratio set by the second setting means.

7. A system as in claim 3, wherein said control means includes means for, in sequence:
   (a) controlling the transmitting means to transmit an ultrasound beam to the subject in a first direction;
   (b) controlling the transmitting means to transmit ultrasound beams to the subject in additional direction, including a second direction through a direction equal to said detection ratio; and
   (c) repeating said steps (a) and (b) a number of times equal to said generation interval.

* * * * *